US007141695B2

(12) United States Patent
Przewosny et al.

(10) Patent No.: US 7,141,695 B2
(45) Date of Patent: Nov. 28, 2006

(54) METHODS FOR PRODUCING SUBSTITUTED ACRYLIC ACID ESTERS AND USE OF THE LATTER FOR PRODUCING SUBSTITUTED γ-AMINO ACIDS

(75) Inventors: Michael Thomas Przewosny, Aachen (DE); Claudia Pütz, Düren (DE)

(73) Assignee: Grunenthal GmbH, Aachen (DE)

( * ) Notice: Subject to any disclaimer, the term of this patent is extended or adjusted under 35 U.S.C. 154(b) by 237 days.

(21) Appl. No.: 10/894,389

(22) Filed: Jul. 19, 2004

(65) Prior Publication Data

US 2005/0043565 A1    Feb. 24, 2005

Related U.S. Application Data

(63) Continuation of application No. PCT/EP03/00213, filed on Jan. 11, 2003.

(30) Foreign Application Priority Data

Jan. 25, 2002  (DE)  ............................... 102 03 122

(51) Int. Cl.
*C07C 229/00* (2006.01)
(52) U.S. Cl. ...................... 560/125; 560/172; 562/507; 562/530
(58) Field of Classification Search .................... None
See application file for complete search history.

(56) References Cited

FOREIGN PATENT DOCUMENTS

| DE | 39 28 182 | 2/1991 |
| DE | 692 04 929 | 3/1996 |
| WO | WO 98/17627 | 4/1998 |
| WO | WO 99/14184 | 3/1999 |

OTHER PUBLICATIONS

Gomez-Monterrey et al., "Exploration of Neutral Endopeptidase Active Site by a Series of New Thiol-Containing Inhibitors", J. Med. Chem., 1993, 36, pp. 87-94.
Barbot et al., "Addition en 1,8 d'organocuprates lithiens satures sur la cetone $CH_3(CH=CH)_3COCH_3$ et sur l'ester $CH_3(CH=CH)_3COCH_3COOC_2H_5$", Journal of Organometallic Chemistry, 345, 1988, pp. 239-243.
Vasil'ev et al., "A Versatile and Convenient Protocol for the Stereocontrolled Synthesis of Olefinic Insect Pheromones", Bioorganic & Medicinal chemistry, vol. 4, No. 3, 1996, pp. 389-400.
Villieras, et al., "Witiig-Horner Reactions in Heterogeneous Media; $2^1$.A Convenient Synthesis of a,β-Unsaturadted esters and Ketones using Weak Bases in Water", Synthesis, vol. 4, 1983, pp. 300-303.
Bryans et al., "Identification of Novel Ligands for the Gabapentin Binding Site on the $\alpha_2\delta$ Subunit of a Calcium Channel and Their Evaluation as Anticonvulsant Agents", J. Med. Chem., 1998, 41, pp. 1838-1845.
"Pregabalin", L. Martin, et al., Drugs of the Future 1999, 24(8), pp. 862-870.
"Identification of Novel Ligands for the Gabapentin Binding Site on the $\beta_2\delta$ Subunit of a Calcium Channel and Their Evaluation a Anticonvulsant Agents", Justin S. Bryans, et al., J. Med. Chem. 1998, 41, pp. 1838-1845.
"3-Substituted GABA Analogs with Central Nervous System Activity: A Review", Justin S. Bryans, et al., 1999, pp. 149-177.

*Primary Examiner*—Paul A. Zucker
(74) *Attorney, Agent, or Firm*—Perman & Green, LLP

(57) ABSTRACT

The invention relates to methods for producing substituted acrylic acid esters and to the use of the latter for producing substituted γ-amino acids, such as gabapentin and pregabalin. The substituted acrylic acid esters are produced by Wadsworth-Emmons olefination with trialkyl phosphonoacetate in the presence of alkali carbonate as the base, in an aqueous solvent.

11 Claims, No Drawings

METHODS FOR PRODUCING SUBSTITUTED ACRYLIC ACID ESTERS AND USE OF THE LATTER FOR PRODUCING SUBSTITUTED γ-AMINO ACIDS

This application is a continuation of international application number PCT/EP03/00213 filed Jan. 11, 2003, status pending, and claims priority to German Patent Application 102 03 122.3 filed Jan. 25, 2002.

The present invention relates to processes for the production of Substituted acrylic acid esters and the use thereof to produce Substituted γ-amino acids, such as gabapentin and pregabalin.

Substituted γ-amino acids, such as gabapentin of formula (A) below and pregabalin of formula (B) below, are used as medicines for the treatment of epilepsy and pain (J. S. Bryans, D. J. Wustrow; Medicinal Research Reviews 19, 149–177 (1999) and L. Martin, X. Rabasseda, P. Leeson, J. Castaner; Drugs of the Future 24, 862–870 (1999)).

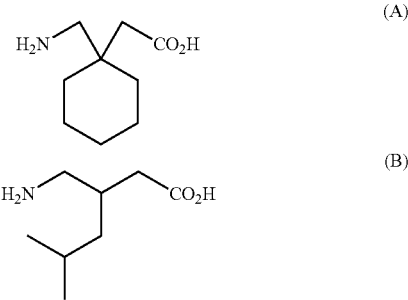

A series of processes for the production of gabapentin and pregabalin are known from the prior art. Reference is made by way of example to a process described by J. S. Bryans et al. (J. Med. Chem. 41, 1838–1845 (1998)) for the production of gabapentin.

In accordance with this process, acrylic acid ethyl esters may be produced from ketones or aldehydes by Wadsworth-Emmons olefination with triethyl phosphonoacetate, in the presence of sodium hydride as base and in tetrahydrofuran as solvent. Nitromethane is then added by Michael Addition. The nitro group is reduced to the amino group, wherein the compounds formed cyclise to yield γ-lactams. The γ-amino acids may be obtained by acidic hydrolysis.

A disadvantage of this known process is the use of alkali metal hydrides for the production of substituted acrylic acid esters in the first reaction stage, which makes it necessary to use absolute organic solvents and to perform the procedure under protective gas.

The object of the present invention was accordingly to improve the first reaction stage for the production of substituted acrylic acid esters in such a way that the procedure may be performed Without absolute organic solvents and without protective gas and high purity substituted acrylic acid esters are obtained in high yields, so simplifying the above-described process for the production of substituted γ-amino acids, such as gabapentin and pregabalin.

According to the invention, the object is achieved by providing the hereinafter described processes for the production of substituted acrylic acid esters and of substituted γ-amino acids produced therefrom, such as gabapentin and pregabalin.

The present invention accordingly provides a process for the production of substituted acrylic acid esters of the genera' formula II,

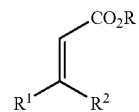

in which
R denotes a linear or branched, saturated or unsaturated aliphatic $C_{1-3}$ residue, preferably an ethyl group,
$R^1$ denotes hydrogen or a linear or branched, saturated or unsaturated aliphatic $C_{1-6}$ residue, preferably a $C_{1-3}$ residue, and
$R^2$ denotes a linear or branched, saturated or unsaturated aliphatic $C_{1-6}$ residue, preferably a $C_{1-4}$ residue, or
$R^1$ and $R^2$ together form a saturated hydrocarbon chain with the formation of a 3–8-membered cycloaliphatic ring, in which
a ketone or aldehyde of the general formula V, in which $R^1$ and $R^2$ have the above-stated meaning,

is reacted with a trialkyl phosphonoacetate of the general formula VI, in which R denotes a linear or branched, saturated or unsaturated aliphatic $C_{1-3}$ residue, preferably an ethyl group,

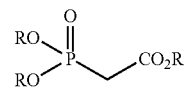

in the presence of alkali metal carbonate, preferably potassium carbonate, in an aqueous solvent, preferably water.

The compounds of the general formulae V and VI together with the alkali metal carbonate, preferably the potassium carbonate, are preferably combined at a temperature in the range from 0 to 10° C., preferably with ice cooling, and reacted at a temperature in the range of ≦25° C., preferably with ice cooling, to yield a substituted acrylic acid ester of the general formula II. The temperature is preferably regulated by ice cooling before and during the reaction.

After the reaction, the substituted acrylic acid ester of the general formula II may be purified, preferably by extraction, wherein diethyl ether is preferred as solvent.

A process is particularly preferred in which cyclohexanone or 3-methylbutanal as a compound of the general formula V is reacted with triethyl phosphonoacetate as a compound of the general formula VI in each case to yield cyclohexylideneacetic acid ethyl ester or 5-methylhex-2-ene carboxylic acid ethyl ester respectively.

High purity substituted acrylic acid esters of the general formula II are obtained in high yields by the process according to the invention. The olefination procedures may be performed both on the 0.5-molar scale and on the multi-molar scale without impairing purity or yield. The substituted acrylic acid esters of the general formula II produced according to the invention may be immediately further reacted after a purity check by GC/MS analysis. As synthesis proceeds for the production of substituted γ-amino acids, the above-listed synthesis steps may be performed without change. With regard to the corresponding production, the disclosure made by J. S. Bryans et al. (J. Med. Chem. 41, 1838–1845 (1998)) is hereby introduced as reference.

The present invention accordingly further provides processes for the production of a substituted γ-amino acid of the general formula I, in which $R^1$ and $R^2$ have the above-stated meaning,

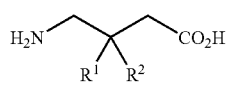

I in which a) a substituted acrylic acid ester of the general formula II, which has been produced by the above-described process according to the invention,

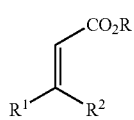

II is reacted under a protective gas atmosphere with the addition of nitromethane to yield a compound of the general formula III, preferably in the presence of tetrabutylammonium fluoride as catalyst in a suitable solvent, preferably tetrahydrofuran,

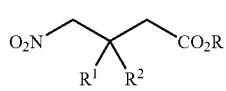

III b) the compound of the general formula III is reduced to yield a lactam of the formula IV, preferably by reaction with hydrogen in the presence of a suitable catalyst, preferably Raney nickel, in a suitable solvent, preferably methanol,

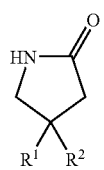

IV c) the lactam of the general formula IV is opened to yield a γ-amino acid of the formula I, preferably by reaction with an acid, preferably hydrochloric acid, in a suitable solvent, preferably dioxane.

A process is particularly preferred in which cyclohexanone or 3-methylbutanal as a compound of the general formula V is reacted with triethyl phosphonoacetate as a compound of the general formula VI in each case to yield cyclohexylideneacetic acid ethyl ester or 5-methylhex-2-ene carboxylic acid ethyl ester respectively in the first reaction stage and is further processed as stated to yield gabapentin or pregabalin respectively.

In the process according to the invention for the production of substituted acrylic acid esters or in the first reaction stage for the production of substituted γ-amino acids, such as gabapentin and pregabalin, alkali metal carbonates are used as the base. Therefore, in the case of Wadsworth-Emmons olefination, it is possible according to the invention to dispense with protective gas and absolute organic solvents, and to use aqueous solvents, preferably water.

Substituted γ-amino acids, such as gabapentin and pregabalin are used as pharmaceutical preparations for the treatment of epilepsy and pain.

The invention is explained below with reference to Examples. These explanations are given merely by way of example and do not restrict the general concept of the invention.

EXAMPLES

The chemicals and solvents used were purchased from conventional suppliers (Acros, Aldrich, Fluka, Lancaster and Merck).

The NMR spectra were measured with spectrometers made by Bruker Analytik GmbH, Silberstreifen 4, D-76287 Rheinstetten. The instrument names are as follows: for 300 MHz: Avance DPX 300 MHz, for 600 MHz: Avance DRX 600 MHz.

GC analysis was performed on an HP 6890 gas chromatograph (with PTV injector) and a 5973 Mass Selective Detector made by Hewlett Packard coupled thereto.

The ESI mass spectra were measured with a Finnigan LCQ model instrument made by Thermoquest, Analytische Systeme GmbH, Boschring 12, D-63329 Egelsbach and evaluated with Xcalibur software.

Example 1

Synthesis of Gabapentin Hydrochloride 1.1. Synthesis of cyclohexylideneacetic acid ethyl ester

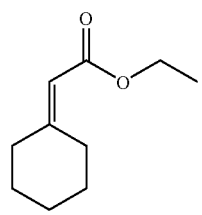

31.1 ml (0.3 mol) of cyclohexanone, 72.1 ml (0.36 mol) of triethyl phosphonoacetate and 83 g (0.6 mol) of potassium carbonate were combined in 60 ml of water with ice cooling and stirred for 20 hours with the temperature slowly being raised to 25° C.

The reaction batch was diluted with 50 ml of water and extracted three times with ether. The organic phase was washed to neutrality with water, dried over MgSO$_4$ and evaporated, and cyclohexylideneacetic acid ethyl ester was obtained as a pale yellowish liquid in a yield of 47.4 g (94% of theoretical).

MS (calculated: 168.34 g/mol): 168 (M$^+$), 153 (M$^+$ —CH$_3$), 139 (M$^+$ —CH$_2$CH$_3$), 123 (M$^+$ —OCH$_2$CH$_3$), 95 (M$^+$—CO$_2$CH$_2$CH$_3$).

$^1$H-NMR (CDCl$_3$/TMS$_{int.}$): δ=1.27 ppm (3H, t, CH$_3$, J=7.2 Hz); 1.64 ppm (6H, m, CH$_2$); 2.19 ppm (2H, m, CH$_2$); 2.83 ppm (2H, m, CH$_2$); 4.14 ppm (2H, q, OCH$_2$, J=7.1 Hz); 5.60 ppm (1H, s, olefin-H).

1.2. Synthesis of (1-nitromethylcyclohexyl)acetic acid ethyl ester

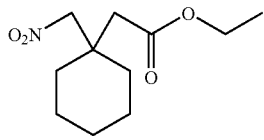

14.8 g (0.088 mol) of the cyclohexylideneacetic acid ethyl ester produced according to 1.1 were dissolved in 50 ml of tetrahydrofuran, 7.11 ml (0.132 mol) of nitromethane and 88 ml of tetrabutylammonium fluoride (1 molar in tetrahydrofuran) were added under a nitrogen atmosphere and refluxed for 20 hours. After cooling, the mixture was diluted with 50 ml of water and extracted three times with dieethyl ether. The organic phase was washed with 10 wt. % aqueous potassium hydrogensulfate solution and then washed with water, dried over magnesium sulfate and evaporated. (1-Nitromethylcyclohexyl)acetic acid ethyl ester was obtained as an orange-yellow oily liquid. The yield amounted to 19.8 g (98% of theoretical).

MS (calculated: 229.28 g/mol): 230 (M$^+$), 184 (M$^+$ —OCH$_2$CH$_3$), 169 (M$^+$ —CH$_2$NO$_2$).

$^1$H-NMR (CDCl$_3$/TMS$_{int.}$): δ=1.27 ppm (3H, t, CH$_3$, J=7.2 Hz); 1.48–1.53 ppm (10, m, CH$_2$); 2.54 ppm (2H, s, CH$_2$); 4.15 ppm (2H, q, OCR$_2$, J=7.2 Hz); 4.71 ppm (2H, s, CR$_2$)

1.3. Synthesis of 2-azaspiro[4.5]decan-3-one

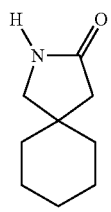

22 g (0.096 mol) of (1-nitronethylcyclohexyl)acetic acid ethyl ester produced according to 1.2. were dissolved in 150 ml of methanol, 2.20 g of Raney nickel were added and hydrogenation was performed for 20 hours with continuous supply of hydrogen. The reaction batch was filtered through diatomaceous earth, rewashed with methanol and evaporated in a rotary evaporator. 15.3 g (100% yield) of a yellowish mass of crystals were obtained.

By stirring with hexane and filtering out, 12.4 g (81% yield) of colourless crystals were obtained.

2-Azaspiro[4.5]decan-3-one was used as crude product for further synthesis.

MS (calculated: 153.22 g/mol): 153 (M$^+$), 125 (M$^+$ —CO), 123 (M$^+$ —CH$_2$NH), 96 (M$^+$ —CH$_2$NHCO), 81 (M$^+$ —CH$_2$NHCOCH$_3$).

$^1$H-NMR (CDCl$_3$/TMS$_{int.}$): δ=1.43 ppm (1OH, m, CH$_2$); 1.98 ppm (2H, s, CH$_2$); 2.99 ppm (2H, s, CH$_2$); 7.20 ppm (1H, s (wide), NH).

1.4. Synthesis of (1aminomethylcyclohexyl)acetic acid hydrochloride (gabapentin hydrochloride)

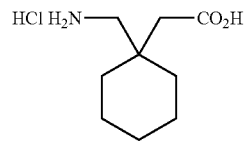

12.4 g (0.81 mol) of the 2-azaspiro[4.5]decan-3-one produced according to 1.3. were redissolved in 4 N hydrochloric acid and stirred for 20 hours at a bath temperature of 110° C. After cooling, the mixture was diluted with water and extracted twice with dichloromethane. The aqueous phase was stirred with activated carbon, filtered through diatomaceous earth, evaporated and dried under a high vacuum. The colourless solid was dissolved in methanol/acetone (5/3, vol./vol.) and precipitated by addition of diethyl ether. After filtering out and washing with diethyl ether, 12.4 g (74% of theoretical) of (1-aminomethylcyclohexyl)acetic acid hydrochloride were obtained.

ESI-MS (calculated: 168.34 g/mol):

$^1$H-NMR (d$_6$-DMSO/TMS$_{ext.}$): δ=1.40 ppm (1OH, m, 5×CH$_2$); 2.40 ppm (2H, m, CH$_2$); 2.90 ppm (2H, m, CH$_2$); 8.00 ppm (3H, s (wide), NH$_3$$^+$); 12.30 ppm (1H, s (wide), CO$_2$H).

Example 2

Synthesis of Pregabalin Hydrochloride 2.1. Synthesis of (2E)-5-methyl-hex-2-ene carboxylic acid ethyl ester

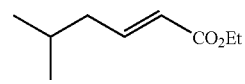

1 mol (138 g) of potassium carbonate was dissolved in 100 ml of water and cooled in ice water. 0.6 mol (120 ml) of phosphonoacetic acid triethyl ester and 0.5 mol (43.1 g) of 3-methylbutanal were added and the mixture was stirred for 20 hours with the temperature slowly being raised to 25° C. The reaction batch was then diluted with 150 ml of water and extracted four times with diethyl ether. The organic phase was dried with magnesium sulfate and evaporated in a rotary evaporator. A clear liquid was obtained. The crude yield amounted to 75.8 g (97% of theoretical).

Gas-chromatographic investigation demonstrated that the crude product contained only traces of the two educts. It was used in the next synthesis stage without further purification steps.

MS (calculated: 156.23 g/mol): 156 (M$^+$), 141 (M$^+$ —CH$_2$), 128 (M$^+$ —CH$_2$CH$_3$), 111 (M$^+$ —OCH$_2$CH$_3$), 86 (M$^+$ —(CH$_3$)$_2$CHCH$_2$)

¹H-NMR (d₆-DMSO/TMS$_{ext.}$) δ=0.89 ppm (6H, d, 2×CH₃, J=6.8 Hz); 1.22 ppm (3H, t, CH₃, J=7.2 Hz); 1.76 ppm (1H, h, CH(CH₃)₂, J=6.5 Hz, J=6.8 Hz); 2.01 ppm (2H, m, CH₂, J=6.8 Hz); 4.11 ppm (2H, q, CH₂O, J=7.2 Hz); 5.83 ppm (1H, dd, CH, J=1.5 Hz, J=15.5 Hz); 6.85 ppm (1H, m, CH), J=7.5 Hz).

2.2. Synthesis of 5-methyl-3-nitromethylhexane carboxylic acid ethyl ester

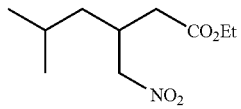

0.485 mol (75.8 g) of the (2E)-5-methyl-hex-2-ene carboxylic acid ethyl ester produced according to 2.1. were dissolved under a nitrogen atmosphere in THF (abs.). 0.73 mol (39.1 ml) of nitromethane and 0.49 mol (485 ml) of a 1 molar tetrabutylammonium fluoride solution in THF were added, wherein an orange solution arose. The mixture was refluxed for 20 hours. After cooling, the mixture was combined with 280 ml of water and extracted four times with diethyl ether. The organic phase was extracted three times with 10% aqueous potassium hydrogensulfate solution and washed to neutrality with water. The organic phase was dried with magnesium sulfate and evaporated in a rotary evaporator. An orange liquid was obtained. The crude yield amounted to 95.2 g (90% of theoretical).

Gas-chromatographic investigation demonstrated that, in addition to 91% product, the crude product contained 7% of tetrabutylammonium fluoride and 2% of unidentifiable secondary product.

For purification, the crude product was stirred for 4 hours in ether and the solution was filtered and evaporated.

MS (calculated: 217.27 g/mol): 202 (M—CH₃), 172 (M—OCH₂CH₃), 156 (M—CH₂NO₂) 143 (M—CO₂CH₂CH₃).

¹H-NMR (d₆-DMSO/TMS$_{ext.}$) δ=0.96 ppm (6H, t, 2×CH₃, J=6.8 Hz); 1.14–1.21 ppm (5H, m, CH₂ and CH₃, J=7.2 Hz); 1.63 ppm (1H, sept, CH, J=6.8 Hz); 2.38 ppm (2H, d, CH₂CO₂Et, J=6.4 Hz); 2.58 ppm (1H, sept, CH, J=6.4 Hz, J=6.8 Hz); 4.07 ppm (2H, q, OCH₂, J=7.0 Hz); 4.55 ppm (2H, d, CH₂NO₂, J=6.4 Hz), 2.3. Synthesis of 4-isobutylpyrrolidin-2-one

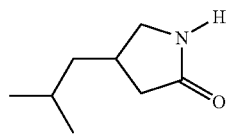

0.39 mol (85.3 g) of the 5-methyl-3-nitromethylhexane carboxylic acid ethyl ester produced and purified according to 2.2. were dissolved in approx. 900 ml of methanol, 25 g of Raney nickel were added and hydrogenation was performed at a temperature of 35° C. and a pressure of 2 bar for 20 hours. The reaction batch was filtered through diatomaceous earth, washed carefully with methanol and evaporated in a rotary evaporator. After drying under a high vacuum, 59.3 g of a colourless liquid were obtained.

MS (calculated: 141.21 g/mol): 141 (M⁺), 126 (M⁺—CH3), 111 (M⁺—CO), 98 (M⁺—CH(CH₃)₂), 84 (M⁺—CH₂NHCOCH₃).

¹H-NMR (d₆-DMSO/TMS$_{ext.}$): δ=0.87 ppm (3H, d, CH₃, J=6,4 Hz), 0.88 ppm (3H, d, CH₃, J=6.4 Hz); 1.28 ppm (2H, t, CH₂, J=7.2 Hz); 1.55 ppm (1H, sept, CH, J=6.4 Hz, 8.8 Hz); 1.79 ppm (1H, dd, CH, J=8.7 Hz); 2.20 ppm (1H, dd, CH, J=8.3 Hz); 2.40 ppm (1H, sept, CH, J=7.5 Hz, J=8.3 Hz); 2.83 ppm (1H, dd, CH, J=7.5 Hz); 3.33 ppm (1H, dd, CH, J=8.3 Hz), 7.46 ppm (s (wide), 1H, NH).

2.4. Synthesis of 3-aminomethyl-5-methylhexanoic acid hydrochloride (pregabalin hydrochloride)

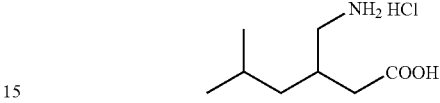

7.16 g (0.06 mol) of the 4-isobutyl-pyrrolidin-2-one produced according to 2.3. were redissolved in 550 ml of 4 N hydrochloric acid and heated for 20 hours at an oil bath temperature of 125° C. After cooling, the mixture was diluted with 500 ml of water and extracted three times with dichloromethane. The aqueous phase was stirred with activated carbon, filtered through diatomaceous earth and evaporated. After drying under a high vacuum, the 3-aminomethyl-5-methyl-hexanoic acid hydrochloride was obtained as an orange-yellow mass of crystals in a yield of 100%.

ESI-MS (calculated: 159.23 g/mol): 160 (MH⁺), 142 (MH⁺—H₂0).

¹H-NMR (d₆-DMSO/TMS$_{ext.}$): δ=0.88 ppm (6H, dd, 2×CH₃) J=Hz); 1.18 ppm (1H, dd, CH₂, J=Hz); 1.20 ppm (1 H, dd, CH₂, J=Hz), 1.61 ppm (1 H, sept, CH, 3=Hz), 2.18 ppm (2H, m, CH₂, J=Hz); 2.45 ppm (1H, dd, CH, J=Hz); 2.78 ppm (2H, m, CH₂, J=Hz); 8.10 ppm (3H, s (wide), NH₃⁺).

What is claimed is:

1. A process for the production of substituted acrylic acid esters of the formula II, in which

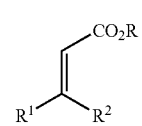

R denotes a linear or branched, saturated or unsaturated aliphatic $C_{1-3}$ group,
R¹ denotes hydrogen or a linear or branched, saturated aliphatic $C_{1-6}$ group and
R² denotes a linear or branched, saturated aliphatic $C_{1-6}$ group, or
R¹ and R² together form a saturated hydrocarbon chain with the formation of a 3–8-membered cycloaliphatic ring,
characterised in that
a ketone or an aldehyde of the formula V, in which R¹ and R² have the above-stated meaning,

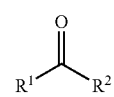

is combined with trialkyl phosphonoacetate of the formula VI, in which R denotes a linear or branched, saturated or unsaturated aliphatic $C_{1-3}$ group,

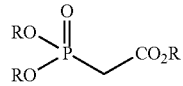

VI and alkali metal carbonate as base in an aqueous solvent at a temperature in the range from 0 to 10° C. and reacted at a temperature in the range of ≦25° C.

2. A process for the production of substituted acrylic acid esters of the formula II, according to claim 1, in which R denotes a linear or branched, saturated or unsaturated aliphatic $C_{1-3}$ group, $R^1$ denotes hydrogen or a linear or branched, saturated or unsaturated aliphatic $C_{1-3}$ group and $R^2$ denotes a linear or branched, saturated or unsaturated aliphatic $C_{1-4}$ group, or $R^1$ and $R^2$ together form a saturated hydrocarbon chain with the formation of a 3–8-membered cycloaliphatic ring.

3. A process according to claim 1, characterised in that a ketone or an aldehyde of the formula V is reacted with trialkyl phosphonoacetate of the formula VI, in which R denotes an ethyl group, in the presence of alkali metal carbonate, in water.

4. A process according to claim 1, characterised in that the combination and/or the reaction, proceed with ice cooling.

5. A process according to claim 1, characterised in that, after the reaction, the substituted acrylic acid ester of the formula II is purified by extraction.

6. A process according to claim 5, characterised in that extraction is performed with diethyl ether.

7. A process according to claim 1, characterised in that cyclohexanone or 3-methylbutanal as a compound of the formula V is reacted with triethyl phosphonoacetate as a compound of the formula VI in each case to yield cyclohexylideneacetic acid ethyl ester or 5-methylhex-2-ene carboxylic acid ethyl ester respectively.

8. A process for the production of a substituted γ-amino acid of the formula I, in which $R^1$ and $R^2$ have the meaning stated in claim 1,

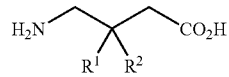

I in which b) a substituted acrylic acid ester of the formula II, in which R, $R^1$ and $R^2$ have the meaning stated in claim 1, is reacted under a protective gas atmosphere with the addition of nitromethane in known manner to yield a compound of the formula III,

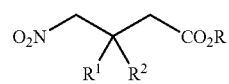

III c) the compound of the formula III is reduced in

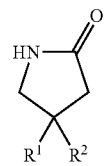

IV known manner to yield a lactam of the formula IV and d) the lactam of the formula IV is cleaved in known manner with the assistance of acid with formation of a substituted γamino acid of the formula I, characterised in that a) the substituted acrylic acid ester of the formula II has been produced using a process according to claim 1.

9. A process according to claim 8, characterised in that cyclohexylideneacetic acid ethyl ester or 5-methylhex-2-ene carboxylic acid ethyl ester obtained by reacting cyclohexanone or 3-methylbutanal as a compound of the formula V with triethyl phosphonoacetate as a compound of the formula VI in each case is reacted to yield gabapentin or pregabalin respectively.

10. A process according to claim 3 where the alkali metal carbonate is potassium carbonate.

11. A process according to claim 4 where the combination and the reaction proceed with ice cooling.

* * * * *